United States Patent [19]

Eick

[11] Patent Number: 5,464,417

[45] Date of Patent: Nov. 7, 1995

[54] APPARATUS AND METHOD FOR SUPPORTING AND CUTTING CORNEA TISSUE

[76] Inventor: Daniel H. Eick, 1136 N. 117th St., Milwaukee, Wis. 53226

[21] Appl. No.: 243,479

[22] Filed: May 16, 1994

[51] Int. Cl.[6] ..................................................... A61B 17/00
[52] U.S. Cl. ................................................................ 606/166
[58] Field of Search ................................ 606/1, 166, 167, 606/184; 269/54.4, 54.5

[56] References Cited

U.S. PATENT DOCUMENTS

| | | |
|---|---|---|
| 3,058,471 | 10/1962 | Shope . |
| 4,342,951 | 8/1982 | Muller et al. . |
| 4,662,370 | 5/1987 | Hoffmann et al. . |
| 4,718,420 | 1/1988 | Lemp . |
| 4,982,969 | 1/1991 | Fedorov et al. . |
| 5,011,498 | 4/1991 | Krumeich et al. . |
| 5,019,084 | 5/1991 | Aysta et al. . |
| 5,092,874 | 3/1992 | Rogers . |
| 5,108,412 | 4/1992 | Krumreich et al. . |

Primary Examiner—Stephen C. Pellegrino
Assistant Examiner—William Lewis
Attorney, Agent, or Firm—Andrus, Sceales, Starke & Sawall

[57] ABSTRACT

A cornea holder for independently holding a predetermined portion of cornea tissue having a corneal button, an endothelial surface and an epithelial surface includes a one-piece, ring-like support member having a bore defining a passageway therethrough. One end of the ring-like member has a plurality of circumferentially spaced support fingers extending inwardly and upwardly therefrom. The support fingers have internally facing bevelled tips diverging outwardly from the passageway to independently support the predetermined portion of cornea tissue endothelial-side up such that the corneal button is suspended in the passageway. A cornea cutting system is also disclosed wherein a rotatable cutting element is moveable through the passageway and engageable solely with the predetermined portion of cornea tissue such that the predetermined portion of cornea tissue is cut along a circumference of the predetermined portion of cornea tissue in a manner which will preserve the number of cells in the endothelial and epithelial surfaces.

14 Claims, 3 Drawing Sheets

5,464,417

APPARATUS AND METHOD FOR SUPPORTING AND CUTTING CORNEA TISSUE

TECHNICAL FIELD

This invention relates generally to apparatus and methods for handling cornea tissue and, more particularly, pertains to an apparatus and method for supporting and cutting a corneal button from a predetermined portion of cornea tissue suitable for implantation in a recipient eye.

BACKGROUND OF THE INVENTION

For purposes of possible transplantation to a recipient eye, the cornea from a donor eye is typically excised in a generally circular section of cornea tissue which is typically subjected to a variety of physical manipulations including a trephining procedure in which a circular corneal button of the desired size is cut out from the corneal tissue for use as a transplant.

It is well known that basic trephining procedures involve the use of cutting blocks and disposable cutting elements in what is commonly known as the "cookie cutter" technique. The cornea tissue is carefully placed epithelial-side down on a block made out of hard inner material such as Teflon, such that the center of the cornea tissue is aligned with the center of the indentation, and the cornea tissue rests in approximately its normal curvature during trephining. A circular metal trephine blade is then carefully aligned and oriented to as to hover above or lightly touch the cornea tissue at the desired, generally central location. The blade is then tapped or turned down into the cornea tissue with sufficient force and to a sufficient distance to cut out a corneal button against the cutting block. Examples of these trephining arrangements are disclosed in U.S. Pat. No. 4,718,420 issued Jan. 12, 1988 to Lemp, U.S. Pat. No. 5,011,498 issued Apr. 30, 1981 to Krumeich et al, U.S. Pat. No. 5,019,084 issued May 28, 1991 to Aysta et al and U.S. Pat. No. 5,092,874 issued Mar. 3, 1992 to Rogers.

These arrangements employing the cookie cutter technique all share a serious drawback in that the inherent cutting action takes place when the trephine blade passes through the cornea material and then hits the Teflon block underneath it causing the sides of the corneal button to be wavy and uneven with major destruction to the endothelial cells. The condition and appearance of the endothelial and epithelial surfaces are critical factors to be determined in deciding whether a particular corneal tissue is suitable for implantation. Abrasions and loss of cells from the endothelial surface are major factors for rejecting many corneal tissues for use and can be attributed at least in part to damage done to the tissue during trephining. An additional problem using the cookie cutter technique occurs when the trephine blade contacts the Teflon block at which time the trephine blade is considered disposable. This means that the trephine blade must be replaced after each cutting operation, which is an unnecessarily costly expense.

Accordingly, it remains desirable to provide an apparatus and method for supporting and cutting a cornea tissue which effectively avoids the disparities and distortions present in prior art devices. It is further desirable to provide a system which provides a centralized cut of corneal button, a reduction in endothelial cell damage, a reusable trephine blade, and a safer handling of the corneal tissue.

SUMMARY OF THE INVENTION

The cornea holder and cutting system of the present invention advantageously provides an effective arrangement for preserving the integrity of endothelial and epithelial cells of a predetermined portion of cornea tissue. The cornea cutting system has a precision construction designed to accurately cut along a circumference of the predetermined portion of cornea tissue without touching the cutting block and the cornea holder.

These and other aspects of the invention are realized in a cornea holder for independently holding a predetermined portion of cornea tissue having a corneal button, an endothelial surface and an epithelial surface. The holder comprises a one-piece, ring-like support member having a bore defining a passageway therethrough, one end of the ring-like member having a plurality of circumferentially spaced support fingers extending inwardly and upwardly therefrom, the support fingers having internally facing beveled tips diverging outwardly from said passageway and adapted to independently support the predetermined portion of cornea tissue endothelial-side up such that the corneal button is suspended in the passageway.

In another aspect of the invention, a cornea cutting system for cutting a corneal button from a cornea portion of cornea tissue having an endothelial surface and an epithelial surface comprises a one-piece, ring-like support member having a bore defining a passageway therethrough, one end of said ring-like member having a plurality of circumferentially spaced support fingers extending inwardly and upwardly therefrom, said support fingers having beveled tips diverging outwardly from said passageway and adapted to support the predetermined portion of cornea tissue endothelial-side up such that the corneal button is suspended in the passageway. A rotatable cutting element is movable through the passageway and is engageable solely with the predetermined portion of cornea tissue such that the predetermined portion of cornea tissue is cut along a circumference of the predetermined portion cornea tissue in a manner which will preserve the number of cells in the endothelial and epithelial surfaces.

In yet another aspect of the invention, a system is contemplated for cutting a predetermined portion of cornea tissue. The system comprises a base having an aperture formed therein and a trephine assembly rotatably and eccentrically mounted on the base about an axis which transverse to the base, the trephine assembly having a rotatable cutting element. A cornea holder is retained in the aperture in the base and has a plurality of circumferentially spaced fingers formed with internally facing chamfers for supporting the predetermined portion of cornea tissue thereon over the aperture. A locking device clamps the trephine assembly in position over the cornea holder whereby the predetermined portion of cornea tissue supported on the cornea holder is cut along a circumference of the predetermined portion of the cornea tissue by the rotatable cutting element without touching the base and the cornea holder.

In yet another aspect of the invention, there is contemplated a method for cutting a corneal button from a predetermined portion of cornea tissue having an endothelial surface and an epithelial surface. The method comprises the steps of providing a one-piece, ring-like cornea holder having a base member formed with an internal passageway therethrough and a plurality of circumferentially spaced fingers formed with upstanding internally facing chamfers; suspending the predetermined portion of cornea tissue endothelial-side up from the fingers such that the corneal button is disposed beneath the chamfers; clamping the predetermined portion of cornea tissue against the fingers of the cornea holder; and rotating a cutting element solely along the passageway until the corneal button of the predetermined portion of corneal tissue is cut along the circumference thereof.

BRIEF DESCRIPTION OF THE DRAWINGS

The invention will become better understood by reference to the following detailed description of the preferred exemplary embodiment when read in conjunction with the appended drawing, wherein like numerals denote like elements

DETAILED DESCRIPTION OF THE PREFERRED EMBODIMENTS

Figure 1:
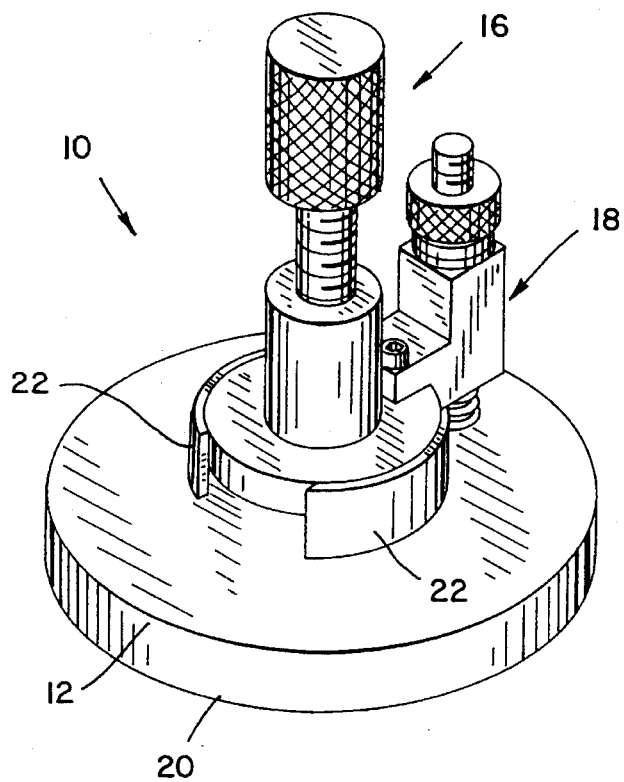
FIG. 1 is a perspective view of the cornea cutting system embodying the present invention depicting a final operating position.

Referring now to FIGS. 1–4, an apparatus 10 for supporting and cutting cornea tissue comprises a base 12, a cornea holder 14, a trephine assembly 16 and a locking device 18. The apparatus is a portable appliance and is constructed principally of surgical grade stainless steel which can be sterilized in an autoclave or sterilized with gas.

Base 12 is a generally circular disk having a flat, planar lower face 20 which will rest firmly on a flat surface. A pair of upstanding, arcuate flanges 22 are provided on base 12 to flank or otherwise partially surround an aperture 24 formed centrally in base 12. Aperture 24 has a recessed or stepped portion 26 which enables cornea holder 14 to be removably supported therein. Cornea holder 14 comprises a one-piece, ring-like support member 30 having a bore 32 defining a passageway therethrough which is adapted to be in communication with aperture 24. One end of cornea holder 14 has a plurality of circumferentially spaced support fingers 34 extending inwardly and upwardly therefrom. Support fingers 34 have internally facing, bevelled or chamfered tips 36 diverging outwardly from passageway 32 and adapted to independently support a predetermined portion of cornea tissue 38 endothelial-side up (epithelial-side down) such that a corneal button 40 is suspended in the passageway 32 beneath tips 36.

Trephine assembly 16 is rotatably and eccentrically mounted on base 12 about an axis transverse thereto and is adapted to be disposed directly over cornea holder 14 seated in base 12. Trephine assembly 16 includes a circular clamping platform 42 moveable upwardly and downwardly within flanges 22. Clamping platform 42 has a central opening 44 surrounded by an upper portion 46 to which is threadably connected a cylindrical cutting head 48 which, in turn, threadably receives a threaded shaft 50. The upper end of shaft 50 is provided with a cylindrical thumbscrew 52 while the lower end of shaft carries a rotatable, generally cylindrical, disposable trephine cutting element 54 which projects from the bottom of cutting head 48 into opening 44 in clamping platform 42. As will be appreciated hereafter, turning of thumbscrew 52 will effectively move cutting element 54 towards and away from cornea holder 14.

Figure 4:
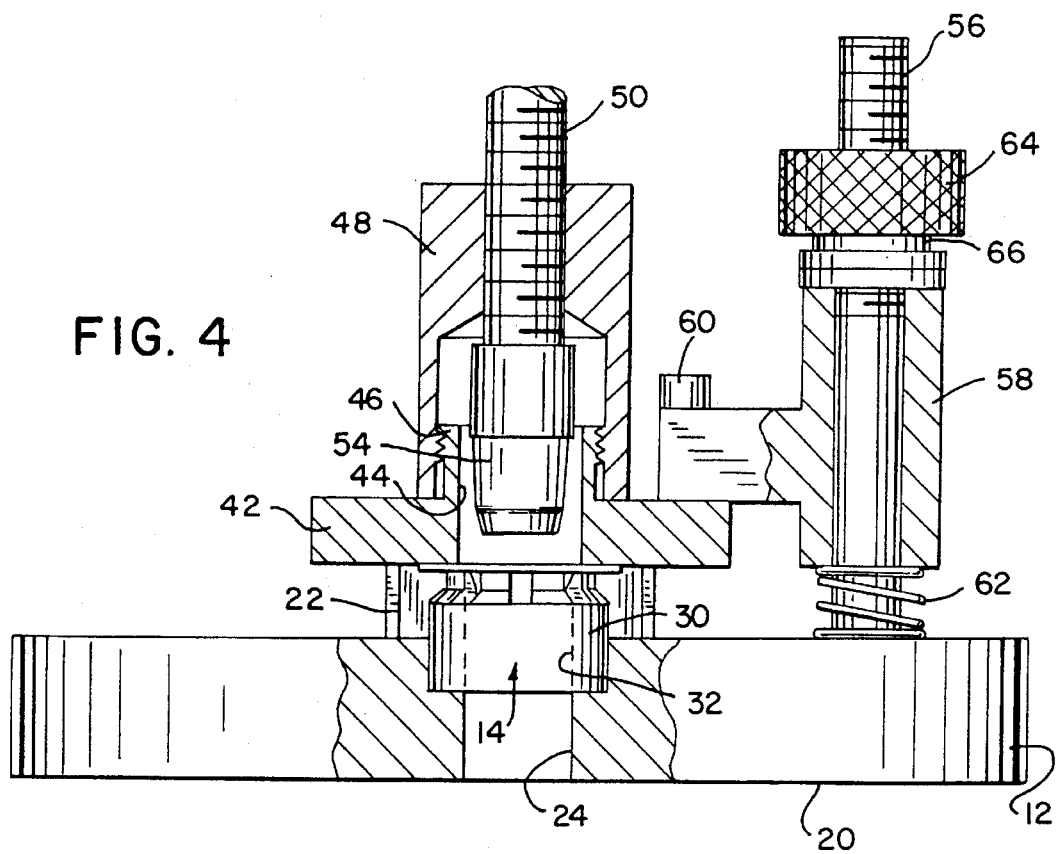
FIG. 4 is a cross-sectional view of the cornea cutting system shown in FIG. 1.
Figure 5:
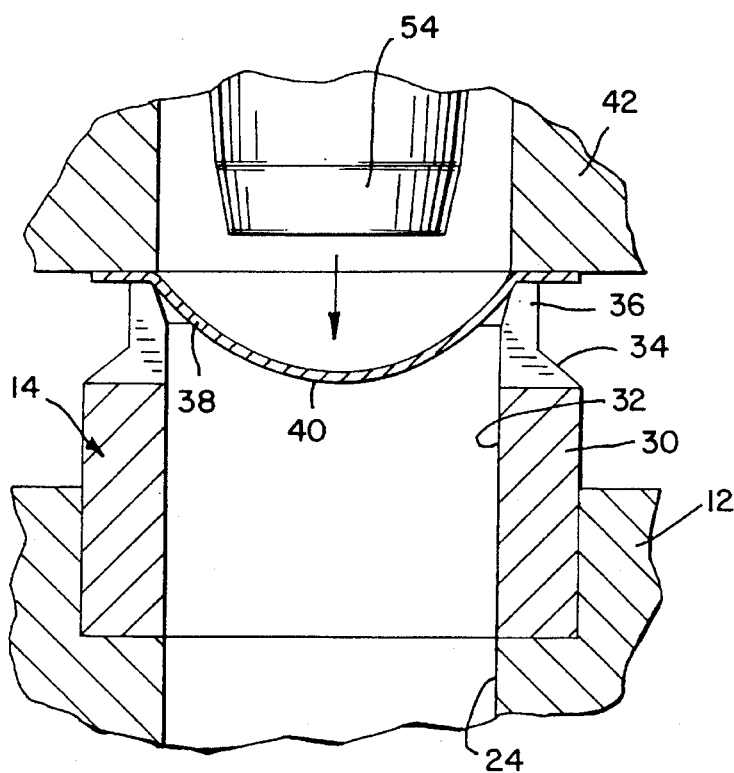
FIG. 5 is an enlarged detail view of a corneal button about to be cut from a predetermined portion of cornea tissue suspended in a cornea holder.

Locking device 18 is provided to swing and lockingly align trephine assembly 16 in place with respect to cornea holder 14. Locking device 18 includes an upstanding rod 56 screwthreaded into and mounted perpendicularly to base 12. A rotatable bracket 58 is fixedly attached by fasteners 60 to clamping platform 42 and is slidably mounted for vertical as well as rotary movement on upstanding rod 56. A coil spring 62 surrounds the lower portion of upstanding rod 56 and is disposed between rotatable bracket 58 and base 12 to normally bias rotatable bracket 58 upwardly. A positioning ring 64 is screwthreaded to the upper portion of upstanding rod 56 and with a plastic washer 66 acts against the top of rotatable bracket 58. With locking device 18, clamping platform 42 is swung into and out of alignment with flanges 22 and raised and lowered with respect thereto by turning positioning ring 64 upwardly and downwardly relative to coil spring 62. In order to produce corneal button 40, clamping platform 42 is lowered and locked against cornea tissue 38 suspended on cornea holder 14 via positioning ring 64 (FIGS. 4–5). This movement automatically aligns cutting element 54 so that turning of thumbscrew 52 will rotate cutting element 54 to move solely along passageway 32 of cornea holder 14 and accurately cut predetermined portion of cornea tissue 38 along a circumference thereof without touching base 12 or cornea holder 14.

Figure 2:
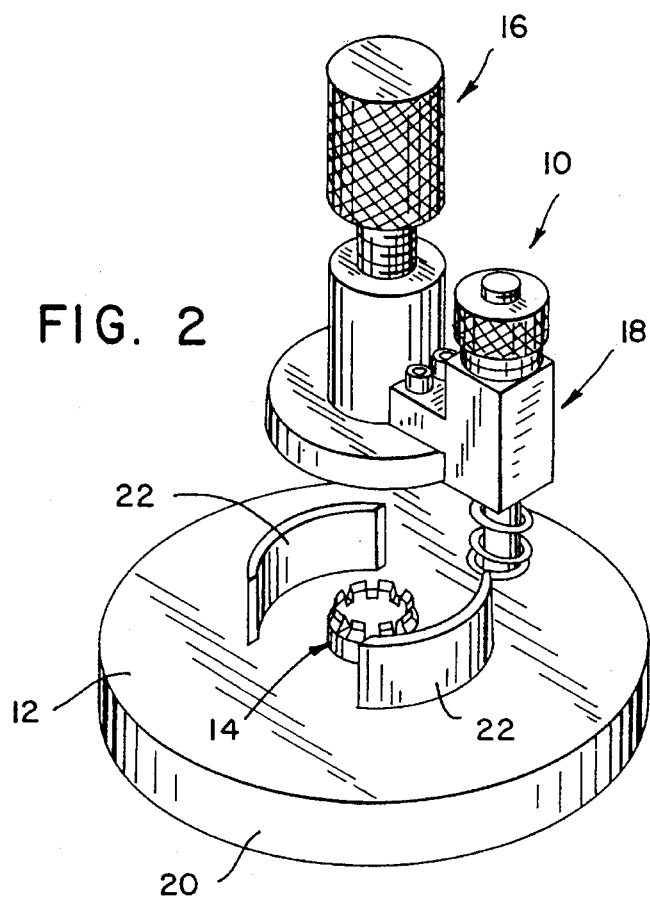
FIG. 2 is a perspective view of the cornea cutting system depicting a beginning operation position.
Figure 3:
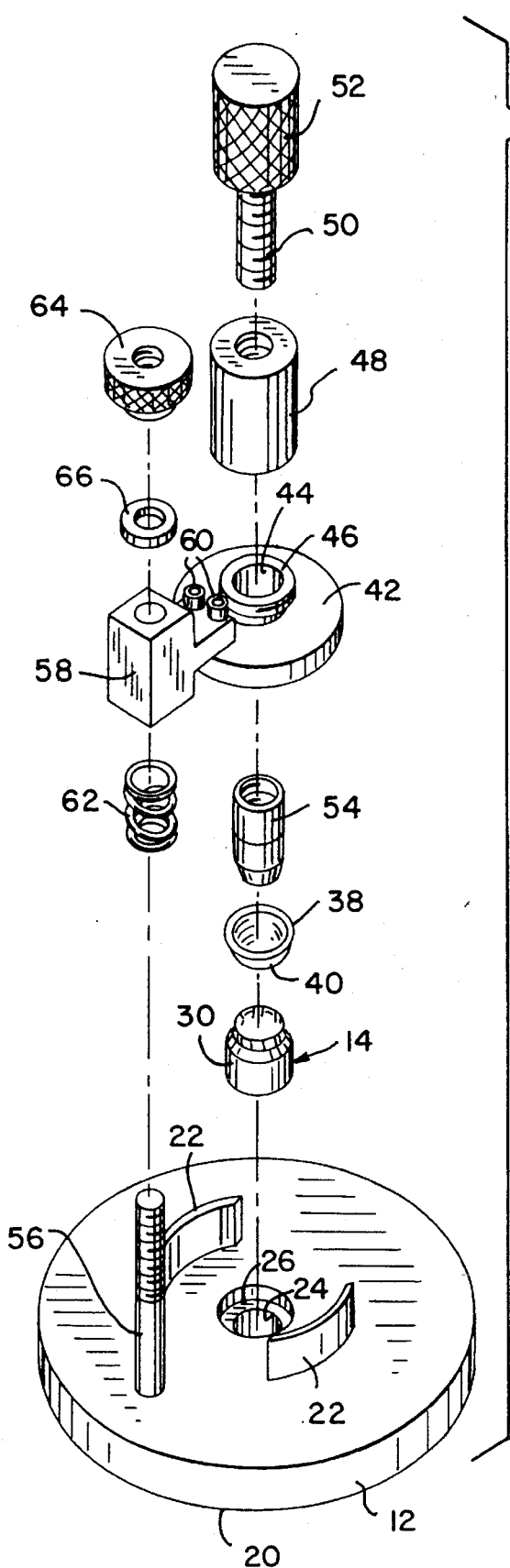
FIG. 3 is an exploded view of the cornea cutting system.
Figure 6:
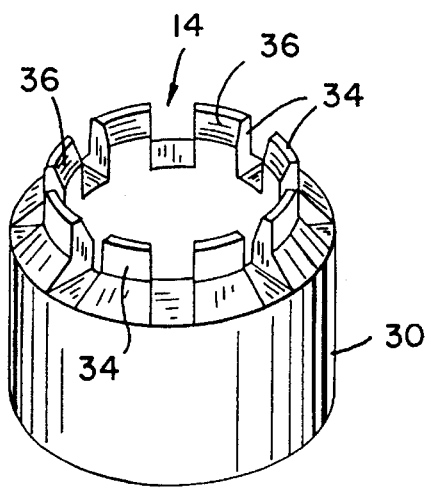
FIG. 6 is an enlarged, perspective view of a cornea holder used in the system.
Figure 7:
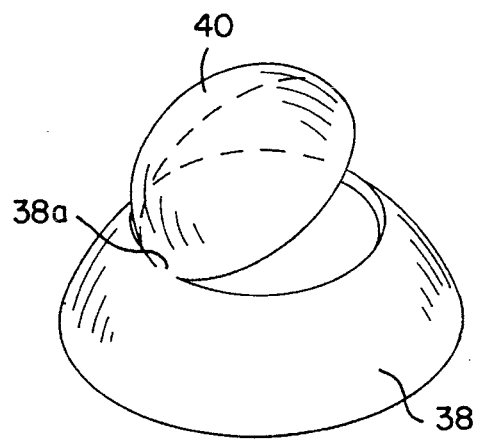
FIG. 7 is an enlarged, perspective view of a corneal button cut from a predetermined portion of cornea tissue.

In use, an eyeball removed from a cadaver is stored in a preservative solution. At the time of implant, the eyeball is taken from storage and laid in a sterile area. The upper one-third portion of the eyeball is carefully removed with a scissors or knife to produce a predetermined portion of cornea tissue 38. With the system as shown in FIG. 2, this tissue 38 is then placed on the tips 36 of support fingers 34 of cornea holder 14 endothelial-side up using a forceps or tweezers. After centering cornea tissue 38 on cornea holder 14 such that the corneal button 40 is independently suspended in passageway 32, trephine assembly 16 is rotated over and moved downwardly onto the cornea tissue 38 with positioning ring 64 locking clamping platform 42 in place over cornea holder 14 as shown in FIG. 1. Unscrewing cutting head 48 from clamping platform 42, the desired trephine blade or cutting element 54 is then chosen and threaded onto shaft 50 and retracted for safety into cutting head 48 by turning thumbscrew 52. Cutting head 48 is then screwed back on clamping platform 42 and thumbscrew 52 is turned to precisely rotate and move cutting element 54 downwardly solely through passageway 32 to cut the predetermined position of cornea tissue 38 along a circumference thereof without touching base 12 or cornea holder 14. As a result, a corneal button 40 is produced with a maximum amount of undamaged endothelial cells ready for transplantation. In some cases, corneal button 40 is retained in cutting element 54 and is freed by depositing a small amount of collagen or the like using a cotton tip applicator. More often, corneal button 40 remains attached by a thin strand 38a (FIG. 7) of cornea tissue 38 which is snipped by a scissors so that corneal button 40 is transferred by forceps or the like to the recipient's eye.

It should be appreciated that the rotary movement combined with the traversal of cutting element 54 solely through passageway 32 without touching any other foreign support structure enables a highly accurate trephining operation which produces a corneal button 40 having a maximized amount of healthy cells conducive to acceptance as transplant material. Furthermore, because of the elimination of a trephining block, the present invention provides that cutting element 54 may be reused for as many as 20–30 times before being replaced. This advantage results in a significant savings in both time spent replacing cutting element 40 and in the cost of the cutting element 40 itself. It should likewise be understood that the design of cornea holder 14 is crucial to the proper suspension of cornea tissue 38. While clamping platform 42 affects the cornea tissue 38 as it is clamped against cornea holder 14, the precious corneal button 40 is safely isolated in suspension, its periphery cleanly cut by the rotary motion of cutting element 54.

While the invention has been described with reference to a preferred embodiment, those skilled in the art will appreciate that certain substitutions, alterations and omissions may be made without departing from the spirit thereof. Accordingly, the foregoing description is meant to be exemplary only, and should not be deemed limitative on the scope of the invention set forth with the following claims.

I claim:

1. A system for cutting a predetermined portion of cornea tissue, said system comprising:

a base having an aperture formed therein;

a trephine assembly rotatably and eccentrically mounted on said base about an axis which is transverse to said base, said trephine assembly having a rotatable cutting element;

a cornea holder retained in said aperture in said base and having a plurality of circumferentially spaced fingers formed with internally facing chamfers for supporting the predetermined portion of cornea tissue thereon over said aperture; and a locking device clamping said trephine assembly in position over said cornea holder whereby the predetermined portion of cornea tissue supported on said cornea holder is cut along a circumference of the predetermined portion of the cornea tissue by said rotatable cutting element without touching said base and said cornea holder.

2. The system of claim 1, wherein said base includes a pair of upstanding arcuate flanges.

3. The system of claim 2, wherein said trephine assembly comprises a clamping platform engageable with said flanges.

4. The system of claim 3, wherein said trephine assembly further comprises a cutting head threadably connected to said clamping platform.

5. The system of claim 4, wherein said trephine assembly comprises a threaded shaft threadably connected to said cutting head.

6. The system of claim 5, wherein said threaded shaft has a thumbscrew at an upper end and said cutting element is mounted on a lower end.

7. The system of claim 3, wherein said locking device includes a rotatable bracket connected with said clamping platform.

8. The system of claim 7, wherein said locking device includes an upstanding rod mounted perpendicular to said base, said upstanding rod having a threaded lower end and a threaded upper end.

9. The system of claim 8, wherein said rotatable bracket is moveable upwardly and downwardly along and swingable about said upstanding rod.

10. The system of claim 8, including a coil spring mounted on said upstanding rod between said base and said rotatable bracket.

11. The system of claim 1, wherein said clamping platform is engageable with said predetermined portion of cornea tissue.

12. The system of claim 8, wherein said locking device includes a positioning ring threadably connected on said upper end of said upstanding rod and engageable with said rotatable bracket.

13. A method for cutting a corneal button from a predetermined portion of cornea tissue having an endothelial surface and an epithelial surface comprising the steps of:

providing a one-piece, ring-like cornea holder having a base member formed with an internal passageway therethrough and a plurality of circumferentially spaced fingers formed with upstanding, internally facing chamfers;

suspending said predetermined portion of cornea tissue endothelial-side up from said fingers such that said corneal button is disposed beneath said chamfers;

clamping the predetermined portion of cornea tissue against said fingers of said cornea holder; and rotating a cutting element solely along said passageway until said corneal button of said predetermined portion of corneal tissue is cut along the circumference thereof.

14. A method of cutting a corneal button from a predetermined portion of cornea tissue having an endothelial surface and an epithelial surface, the method comprising the steps of:

placing the predetermined portion of cornea tissue endothelial side up on a one piece, ring-like support member having a bore defining a passageway therethrough, one end of said ring-like member having a plurality of circumferentially spaced support fingers extending inwardly and upwardly therefrom, the support fingers having bevelled tips diverging outwardly from said passageway and adapted to support the cornea tissue such that the corneal button is suspended in said passageway; and moving a rotatable cutting element through said passageway so that it is engageable solely with the predetermined portion of cornea tissue such that the predetermined portion of cornea tissue is cut along a circumference of the predetermined portion of cornea tissue in a manner which will preserve the number of cells in the endothelial and epithelial surfaces.

* * * * *